(12) United States Patent
An et al.

(10) Patent No.: US 7,741,042 B2
(45) Date of Patent: Jun. 22, 2010

(54) METHOD FOR PREPARING A DNA CHIP AND USE THEREOF

(75) Inventors: Sung-Whan An, Taejeon (KR);
Chi-Wang Yoon, Taejeon (KR);
Tae-Jeong Oh, Taejeon (KR);
Dae-Kyung Yoon, Taejeon (KR);
Sun-Woo Lee, Taejeon (KR);
Myung-Soon Kim, Taejeon (KR);
Suk-Kyung Woo, Taejeon (KR); Keun Ha Kim, Taejeon (KR)

(73) Assignee: Genomictree, Inc., Taejeon (KR)

( * ) Notice: Subject to any disclaimer, the term of this patent is extended or adjusted under 35 U.S.C. 154(b) by 206 days.

(21) Appl. No.: 11/578,634

(22) PCT Filed: Apr. 19, 2004

(86) PCT No.: PCT/KR2004/000894

§ 371 (c)(1),
(2), (4) Date: Oct. 17, 2006

(87) PCT Pub. No.: WO2005/100598

PCT Pub. Date: Oct. 27, 2005

(65) Prior Publication Data

US 2007/0224605 A1    Sep. 27, 2007

(51) Int. Cl.
*C12Q 1/68* (2006.01)
*C12P 21/06* (2006.01)
*C12P 19/34* (2006.01)

(52) U.S. Cl. .............. 435/6; 435/5; 435/69.1; 435/91.1; 435/91.4; 435/91.52; 536/23.1; 536/24.2

(58) Field of Classification Search .......... 435/5, 435/69.1, 91.2, 91.4, 91.52; 535/23.1, 24.3
See application file for complete search history.

(56) References Cited

U.S. PATENT DOCUMENTS

| 5,681,726 A | * | 10/1997 | Huse et al. ............ 435/91.52 |
| 5,705,627 A | | 1/1998 | Manos et al. |
| 6,228,577 B1 | | 5/2001 | Mahony et al. |
| 2003/0073081 A1 | * | 4/2003 | Mukai et al. ............ 435/6 |

FOREIGN PATENT DOCUMENTS

| EP | 1 279 733 A1 | 1/2003 |
| KR | 20010091450 A | 10/2001 |
| KR | 10-2004-0036318 | 4/2004 |
| WO | WO-01/68915 A1 | 9/2001 |
| WO | 03020975 A2 | 3/2003 |
| WO | WO-03/083142 A2 | 10/2003 |

OTHER PUBLICATIONS

Oh, Taejong et al. , "Development and Clinical Evaulation of a Highly Sensitive DNA Microrray for Detection and Genotyping of Human . . . ", "Journal of Clinical Microbiology", Jul. 2004, pp. 3272-3280, vol. 42, No. 7.

Liu, Cui-Hua, et al., Possibility of Using DNA Chip Technology for Diagnosis of Human Papillomavirus , J. Biochem. Mol. Biol., Jul. 2003, pp. 349-353, vol. 36, No. 4.

* cited by examiner

*Primary Examiner*—Stephen Kapushoc
*Assistant Examiner*—Narayan K Bhat
(74) *Attorney, Agent, or Firm*—Steven J. Hultquist; Kelly K. Reynolds; Intellectual Proper Technology Law

(57) ABSTRACT

The present invention relates to a method for producing a DNA chip, which comprises the steps of: (a) cloning a probe, where a linker is coupled to one or both ends of an oligonucleotide to be integrated on a slide, into a vector; (b) transforming host cells with the vector; (c) culturing the transformed host cells, to recover the probe where the linker is coupled to one or both ends of the oligonucleotides; and (d) integrating the recovered double-helical probes on a slide. Also, the present invention relates to a DNA chip for HPV diagnosis produced by the method, and a method for diagnosing the presence or genotype of HPV using the DNA chip.

9 Claims, 7 Drawing Sheets

SEQUENCE LISTING

<160> NUMBER OF SEQ ID NOS: 60

<210> SEQ ID NO 1
<211> LENGTH: 60
<212> TYPE: DNA
<213> ORGANISM: Artificial
<220> FEATURE:
<223> OTHER INFORMATION: Probe

<400> SEQUENCE: 1
ccaacatgac attatgtgca tccgtaacta catcttccac atacaccaat tctgattata    60

<210> SEQ ID NO 2
<211> LENGTH: 60
<212> TYPE: DNA
<213> ORGANISM: Artificial
<220> FEATURE:
<223> OTHER INFORMATION: Probe

<400> SEQUENCE: 2
tataatcaga attggtgtat gtggaagatg gatttacgga tgcacataat gtcatgttgg    60

<210> SEQ ID NO 3
<211> LENGTH: 60
<212> TYPE: DNA
<213> ORGANISM: Artificial
<220> FEATURE:
<223> OTHER INFORMATION: Probe

<400> SEQUENCE: 3
tatgacacta tgtgcatctg tgtctaaatc tgctacatac actaattcag attataagga    60

<210> SEQ ID NO 4
<211> LENGTH: 60
<212> TYPE: DNA
<213> ORGANISM: Artificial
<220> FEATURE:
<223> OTHER INFORMATION: Probe

<400> SEQUENCE: 4
tccttataat ctgaattagt gtatgtagca gatttagaca cagatgcaca tagtgtcata    60

<210> SEQ ID NO 5
<211> LENGTH: 60
<212> TYPE: DNA
<213> ORGANISM: Artificial
<220> FEATURE:
<223> OTHER INFORMATION: Probe

<400> SEQUENCE: 5
acgcagtaca aatatgtcat tatgtgctgc catatctact tcagaaacta catataaaaa    60

<210> SEQ ID NO 6
<211> LENGTH: 60
<212> TYPE: DNA
<213> ORGANISM: Artificial
<220> FEATURE:
<223> OTHER INFORMATION: Probe

<400> SEQUENCE: 6
tttttatatg tagtttctga agtagatatg gcagcagata atgacatatt tgtacthcgt    60

<210> SEQ ID NO 7
<211> LENGTH: 60
<212> TYPE: DNA
<213> ORGANISM: Artificial
<220> FEATURE:
<223> OTHER INFORMATION: Probe

<400> SEQUENCE: 7
caatttaaca atatgtgctt ctacacagtc tcctgtacct gggcaatatg atgctaccaa    60

<210> SEQ ID NO 8
<211> LENGTH: 60
<212> TYPE: DNA
<213> ORGANISM: Artificial
<220> FEATURE:
<223> OTHER INFORMATION: Probe -continued

```
<400> SEQUENCE: 8
ttggtagcat catattgccc aggtacagga gactgtgtag aagcacatat tgttaaattg      60

<210> SEQ ID NO 9
<211> LENGTH: 60
<212> TYPE: DNA
<213> ORGANISM: Artificial
<220> FEATURE:
<223> OTHER INFORMATION: Probe

<400> SEQUENCE: 9
tagtaccaat atgtctgttt gtgctgcaat tgcaaacagt gatactacat ttaaaagtag      60

<210> SEQ ID NO 10
<211> LENGTH: 60
<212> TYPE: DNA
<213> ORGANISM: Artificial
<220> FEATURE:
<223> OTHER INFORMATION: Probe

<400> SEQUENCE: 10
ctacttttaa atgtagtatc actgtttgca attgcagcac aaacagacat attggtacta      60

<210> SEQ ID NO 11
<211> LENGTH: 60
<212> TYPE: DNA
<213> ORGANISM: Artificial
<220> FEATURE:
<223> OTHER INFORMATION: Probe

<400> SEQUENCE: 11
cagtactaat atgactttat gcacacaagt aactagtgac agtacatata aaatgaaaa      60

<210> SEQ ID NO 12
<211> LENGTH: 60
<212> TYPE: DNA
<213> ORGANISM: Artificial
<220> FEATURE:
<223> OTHER INFORMATION: Probe

<400> SEQUENCE: 12
ttttcatttt tatatgtact gtcactagtt acttgtgtgc ataaagtcat attagtactg      60

<210> SEQ ID NO 13
<211> LENGTH: 60
<212> TYPE: DNA
<213> ORGANISM: Artificial
<220> FEATURE:
<223> OTHER INFORMATION: Probe

<400> SEQUENCE: 13
ttcagtttgt gtaggtacac aatccacaag tacaactgca ccatatgcaa acagtaattt      60

<210> SEQ ID NO 14
<211> LENGTH: 60
<212> TYPE: DNA
<213> ORGANISM: Artificial
<220> FEATURE:
<223> OTHER INFORMATION: Probe

<400> SEQUENCE: 14
aaattactgt ttgcatatgg tgcagttgta cttgtggatt gtgtacctac acaaactgaa      60

<210> SEQ ID NO 15
```

```
<211> LENGTH: 60
<212> TYPE: DNA
<213> ORGANISM: Artificial
<220> FEATURE:
<223> OTHER INFORMATION: Probe

<400> SEQUENCE: 15
ccgtagtaca aatatgtctg tgtgttctgc tgtgtcttct agtgacagta catataaaaa      60

<210> SEQ ID NO 16
<211> LENGTH: 60
<212> TYPE: DNA
<213> ORGANISM: Artificial
<220> FEATURE:
<223> OTHER INFORMATION: Probe

<400> SEQUENCE: 16
tttttatatg tactgtcact agaagacaca gcagaacaca cagacatatt tgtactacgg      60

<210> SEQ ID NO 17
<211> LENGTH: 60
<212> TYPE: DNA
<213> ORGANISM: Artificial
<220> FEATURE:
<223> OTHER INFORMATION: Probe

<400> SEQUENCE: 17
accaacttta cattatctac ctctatagag tcttccatac cttctacata tgatccttct      60

<210> SEQ ID NO 18
<211> LENGTH: 60
<212> TYPE: DNA
<213> ORGANISM: Artificial
<220> FEATURE:
<223> OTHER INFORMATION: Probe

<400> SEQUENCE: 18
agaaggatca tatgtagaag gtatggaaga ctctatagag gtagataatg taaagttggt      60

<210> SEQ ID NO 19
<211> LENGTH: 60
<212> TYPE: DNA
<213> ORGANISM: Artificial
<220> FEATURE:
<223> OTHER INFORMATION: Probe

<400> SEQUENCE: 19
aatttaacct tatgtgctgc cacacagtcc cccacaccaa ccccatataa taacagtaat      60

<210> SEQ ID NO 20
<211> LENGTH: 60
<212> TYPE: DNA
<213> ORGANISM: Artificial
<220> FEATURE:
<223> OTHER INFORMATION: Probe

<400> SEQUENCE: 20
attactgtta ttatatgggg ttggtgtggg ggactgtgtg gcagcacata aggttaaatt      60

<210> SEQ ID NO 21
<211> LENGTH: 60
<212> TYPE: DNA
<213> ORGANISM: Artificial
<220> FEATURE:
<223> OTHER INFORMATION: Probe

<400> SEQUENCE: 21
```
tgactttgtg tgccactgca acatctggtg atacatatac agctgctaat tttaaggaat      60

<210> SEQ ID NO 22
<211> LENGTH: 60
<212> TYPE: DNA
<213> ORGANISM: Artificial
<220> FEATURE:
<223> OTHER INFORMATION: Probe

<400> SEQUENCE: 22
attccttaaa attagcagct gtatatgtat caccagatgt tgcagtggca cacaaagtca      60

<210> SEQ ID NO 23
<211> LENGTH: 60
<212> TYPE: DNA
<213> ORGANISM: Artificial
<220> FEATURE:
<223> OTHER INFORMATION: Probe

<400> SEQUENCE: 23
ttgacgttat gtgcctctac tgaccctact gtgcccagta catatgacaa tgcaaagttt      60

<210> SEQ ID NO 24
<211> LENGTH: 60
<212> TYPE: DNA
<213> ORGANISM: Artificial
<220> FEATURE:
<223> OTHER INFORMATION: Probe

<400> SEQUENCE: 24
aaactttgaa ttgtcatatg tactgggcac agtagggtca gtagaggcac ataacgtcaa      60

<210> SEQ ID NO 25
<211> LENGTH: 60
<212> TYPE: DNA
<213> ORGANISM: Artificial
<220> FEATURE:
<223> OTHER INFORMATION: Probe

<400> SEQUENCE: 25
atgacaatat gtgctgccac tacacagtcc cctccgtcta catatactag tgaacaatat      60

<210> SEQ ID NO 26
<211> LENGTH: 60
<212> TYPE: DNA
<213> ORGANISM: Artificial
<220> FEATURE:
<223> OTHER INFORMATION: Probe

<400> SEQUENCE: 26
atattgttca ctagtatatg tagacggagg ggactgtgta gtggcagcac atattgtcat      60

<210> SEQ ID NO 27
<211> LENGTH: 60
<212> TYPE: DNA
<213> ORGANISM: Artificial
<220> FEATURE:
<223> OTHER INFORMATION: Probe

<400> SEQUENCE: 27
acattatgtg cctctacaca aaatcctgtg ccaagtacat atgaccctac taagtttaag      60

<210> SEQ ID NO 28
<211> LENGTH: 60
<212> TYPE: DNA

<213> ORGANISM: Artificial
<220> FEATURE:
<223> OTHER INFORMATION: Probe

<400> SEQUENCE: 28
cttaaactta gtagggtcat atgtacttgg cacaggattt tgtgtagagg cacataatgt    60

<210> SEQ ID NO 29
<211> LENGTH: 60
<212> TYPE: DNA
<213> ORGANISM: Artificial
<220> FEATURE:
<223> OTHER INFORMATION: Probe

<400> SEQUENCE: 29
acaaatttaa ctattagcac tgccactgct gcggtttccc caacatttac tccaagtaac    60

<210> SEQ ID NO 30
<211> LENGTH: 60
<212> TYPE: DNA
<213> ORGANISM: Artificial
<220> FEATURE:
<223> OTHER INFORMATION: Probe

<400> SEQUENCE: 30
gttacttgga gtaaatgttg gggaaaccgc agcagtggca gtgctaatag ttaaatttgt    60

<210> SEQ ID NO 31
<211> LENGTH: 60
<212> TYPE: DNA
<213> ORGANISM: Artificial
<220> FEATURE:
<223> OTHER INFORMATION: Probe

<400> SEQUENCE: 31
taacatgact ttatgtgctg aggttaaaaa ggaaagcaca tataaaaatg aaaattttaa    60

<210> SEQ ID NO 32
<211> LENGTH: 60
<212> TYPE: DNA
<213> ORGANISM: Artificial
<220> FEATURE:
<223> OTHER INFORMATION: Probe

<400> SEQUENCE: 32
ttaaaatttt cattttata tgtgctttcc tttttaacct cagcacataa agtcatgtta    60

<210> SEQ ID NO 33
<211> LENGTH: 60
<212> TYPE: DNA
<213> ORGANISM: Artificial
<220> FEATURE:
<223> OTHER INFORMATION: Probe

<400> SEQUENCE: 33
cctaacattg tgtgctacag catccacgca ggatagcttt aataattctg actttaggga    60

<210> SEQ ID NO 34
<211> LENGTH: 60
<212> TYPE: DNA
<213> ORGANISM: Artificial
<220> FEATURE:
<223> OTHER INFORMATION: Probe

<400> SEQUENCE: 34
tccctaaagt cagaattatt aaagctatcc tgcgtggatg ctgtagcaca caatgttagg    60

<210> SEQ ID NO 35
<211> LENGTH: 60
<212> TYPE: DNA
<213> ORGANISM: Artificial
<220> FEATURE:
<223> OTHER INFORMATION: Probe

<400> SEQUENCE: 35
ctaacatgac tattagtact gctacagaac agttaagtaa atatgatgca cgaaaaatta      60

<210> SEQ ID NO 36
<211> LENGTH: 60
<212> TYPE: DNA
<213> ORGANISM: Artificial
<220> FEATURE:
<223> OTHER INFORMATION: Probe

<400> SEQUENCE: 36 taattttcg tgcatcatat ttacttatct gttctgtagc agtactaata gtcatgttag      60

<210> SEQ ID NO 37
<211> LENGTH: 60
<212> TYPE: DNA
<213> ORGANISM: Artificial
<220> FEATURE:
<223> OTHER INFORMATION: Probe

<400> SEQUENCE: 37
tagcactaat atgacattat gcactgaagt aactaaggaa ggtacatata aaaatgataa      60

<210> SEQ ID NO 38
<211> LENGTH: 60
<212> TYPE: DNA
<213> ORGANISM: Artificial
<220> FEATURE:
<223> OTHER INFORMATION: Probe

<400> SEQUENCE: 38
ttatcatttt tatatgtacc ttccttagtt acttcagtgc ataatgtcat attagtgcta      60

<210> SEQ ID NO 39
<211> LENGTH: 60
<212> TYPE: DNA
<213> ORGANISM: Artificial
<220> FEATURE:
<223> OTHER INFORMATION: Probe

<400> SEQUENCE: 39
ctttctgtgt gtgctctact actctctatt cctaatgtat acacacctac cagttttaaa      60

<210> SEQ ID NO 40
<211> LENGTH: 60
<212> TYPE: DNA
<213> ORGANISM: Artificial
<220> FEATURE:
<223> OTHER INFORMATION: Probe

<400> SEQUENCE: 40
tttaaaactg gtaggtgtgt atacattagg aatagagagt agtagagcac acacagaaag      60

<210> SEQ ID NO 41
<211> LENGTH: 60
<212> TYPE: DNA
<213> ORGANISM: Artificial
<220> FEATURE:

<223> OTHER INFORMATION: Probe

<400> SEQUENCE: 41
tttgtaccgc ctccactgct gcagcagaat acacggctac caactttagg gaattttttgc    60

<210> SEQ ID NO 42
<211> LENGTH: 60
<212> TYPE: DNA
<213> ORGANISM: Artificial
<220> FEATURE:
<223> OTHER INFORMATION: Probe

<400> SEQUENCE: 42
gcaaaaattc cctaaagttg gtagccgtgt attctgctgc agcagtggag gcggtacaaa    60

<210> SEQ ID NO 43
<211> LENGTH: 60
<212> TYPE: DNA
<213> ORGANISM: Artificial
<220> FEATURE:
<223> OTHER INFORMATION: Probe

<400> SEQUENCE: 43
gcagctaaaa gcacattaac taaatatgat gcccgtgaaa tcaatcaata ccttcgccat    60

<210> SEQ ID NO 44
<211> LENGTH: 60
<212> TYPE: DNA
<213> ORGANISM: Artificial
<220> FEATURE:
<223> OTHER INFORMATION: Probe

<400> SEQUENCE: 44
atggcgaagg tattgattga tttcacgggc atcatattta gttaatgtgc ttttagctgc    60

<210> SEQ ID NO 45
<211> LENGTH: 60
<212> TYPE: DNA
<213> ORGANISM: Artificial
<220> FEATURE:
<223> OTHER INFORMATION: Probe

<400> SEQUENCE: 45
tatattctga gggaaaatca gaggctacat acaaaaatga aaactttaag gaatacctta    60

<210> SEQ ID NO 46
<211> LENGTH: 60
<212> TYPE: DNA
<213> ORGANISM: Artificial
<220> FEATURE:
<223> OTHER INFORMATION: Probe

<400> SEQUENCE: 46
taaggtattc cttaaagttt tcattttttgt atgtagcctc tgattttccc tcagaatata    60

<210> SEQ ID NO 47
<211> LENGTH: 60
<212> TYPE: DNA
<213> ORGANISM: Artificial
<220> FEATURE:
<223> OTHER INFORMATION: Probe

<400> SEQUENCE: 47
tgtctactac tactgaatca gctgtaccaa atatttatga tcctaataaa tttaaggaat    60

<210> SEQ ID NO 48
<211> LENGTH: 60
<212> TYPE: DNA
<213> ORGANISM: Artificial
<220> FEATURE:
<223> OTHER INFORMATION: Probe

<400> SEQUENCE: 48
attccttaaa tttattagga tcataaatat ttggtacagc tgattcagta gtagtagaca     60

<210> SEQ ID NO 49
<211> LENGTH: 60
<212> TYPE: DNA
<213> ORGANISM: Artificial
<220> FEATURE:
<223> OTHER INFORMATION: Probe

<400> SEQUENCE: 49
actgtatctg cacaatctgc atctgccact tttaaaccat cagattataa gcagtttata     60

<210> SEQ ID NO 50
<211> LENGTH: 60
<212> TYPE: DNA
<213> ORGANISM: Artificial
<220> FEATURE:
<223> OTHER INFORMATION: Probe

<400> SEQUENCE: 50
tataaactgc ttataatctg atggtttaaa agttgcagat gcagattgtg cagatacagt     60

<210> SEQ ID NO 51
<211> LENGTH: 60
<212> TYPE: DNA
<213> ORGANISM: Artificial
<220> FEATURE:
<223> OTHER INFORMATION: Probe

<400> SEQUENCE: 51
gcctgcaccg aaacggccat acctgctgta tatagcccta caaagtttaa ggaatatact     60

<210> SEQ ID NO 52
<211> LENGTH: 60
<212> TYPE: DNA
<213> ORGANISM: Artificial
<220> FEATURE:
<223> OTHER INFORMATION: Probe

<400> SEQUENCE: 52
agtatattcc ttaaactttg tagggctata tacagcaggt atggccgttt cggtgcaggc     60

<210> SEQ ID NO 53
<211> LENGTH: 60
<212> TYPE: DNA
<213> ORGANISM: Artificial
<220> FEATURE:
<223> OTHER INFORMATION: Probe

<400> SEQUENCE: 53
actgccacag cgtcctctgt atcagaatat acagcttcta attttcgtga gtatcttcgc     60

<210> SEQ ID NO 54
<211> LENGTH: 60
<212> TYPE: DNA
<213> ORGANISM: Artificial
<220> FEATURE:
<223> OTHER INFORMATION: Probe

```
<400> SEQUENCE: 54
gcgaagatac tcacgaaaat tagaagctgt atattctgat acagaggacg ctgtggcagt    60

<210> SEQ ID NO 55
<211> LENGTH: 20
<212> TYPE: DNA
<213> ORGANISM: Artificial
<220> FEATURE:
<223> OTHER INFORMATION: Primer

<400> SEQUENCE: 55
tcaacggatt tggtcgtatt                                                20

<210> SEQ ID NO 56
<211> LENGTH: 20
<212> TYPE: DNA
<213> ORGANISM: Artificial
<220> FEATURE:
<223> OTHER INFORMATION: Primer

<400> SEQUENCE: 56
tagaggcagg gatgatgttc                                                20

<210> SEQ ID NO 57
<211> LENGTH: 23
<212> TYPE: DNA
<213> ORGANISM: Artificial
<220> FEATURE:
<223> OTHER INFORMATION: Primer

<400> SEQUENCE: 57
tttgttactg tggtagatac tac                                            23

<210> SEQ ID NO 58
<211> LENGTH: 25
<212> TYPE: DNA
<213> ORGANISM: Artificial
<220> FEATURE:
<223> OTHER INFORMATION: Primer

<400> SEQUENCE: 58
gaaaaataaa ctgtaaatca tattc                                          25

<210> SEQ ID NO 59
<211> LENGTH: 23
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 59
tttntnachg tdgtdgayac hac                                            23

<210> SEQ ID NO 60
<211> LENGTH: 25
<212> TYPE: DNA
<213> ORGANISM: Artificial
<220> FEATURE:
<223> OTHER INFORMATION: Primer
```

```
<400> SEQUENCE: 60
gaaahataaa ytgyavdtca waytc                                           25
```

METHOD FOR PREPARING A DNA CHIP AND USE THEREOF

CROSS-REFERENCE TO RELATED APPLICATION

This is a filing under the provisions of 35 U.S.C. §371 based on International Patent Application No. PCT/KR2004/000894 filed Apr. 19, 2004 in the names of Sung-Whan AN, et al. for "METHOD FOR PREPARING A DNA CHIP AND USE THEREOF." The disclosure of such International Patent Application is hereby incorporated herein by reference, in its entirety, for all purposes.

TECHNICAL FIELD

The present invention relates to a method for producing a DNA chip using a linker, and a DNA chip for HPV diagnosis produced thereby. More particularly, the present invention relates to a producing method of a DNA chip, which comprises: cloning a probe, where a linker is coupled to an oligonucleotide to be integrated on a slide, into a vector; culturing host cells transformed with the vector, to recover the probe; and integrating the recovered probe on a slide, as well as a DNA chip for HPV diagnosis produced thereby.

BACKGROUND ART

Generally, the production of DNA chips comprises the steps of producing a probe, and integrating the produced probe on a slide. Methods for producing the probe are classified into two categories according to the base sequence length of the probe. Namely, if the probe is an oligonucleotide consisted of 15-25 bases, it is preferably produced by a chemical synthesis method using a synthetic group, etc., but if it is a DNA consisted of more than 100 bases, it is preferably synthesized by PCR amplification. However, the former has a shortcoming that a probe should be produced each time a DNA chip is produced, and the latter has a shortcoming that primers should vary depending on the sequence of a probe.

The present invention aims to provide a producing method of DNA chips, capable of overcoming such prior problems, and to produce DNA chips for the diagnosis of HPV (human papilloma virus) causing cervical cancer.

Cervical cancer refers to cancer that occurs at the uterine cervix. Cervical cancer is the most frequent gynecologic cancer in Korean women (about 6,000 new patients are diagnosed as cervical cancer annually), and is a disease requiring special care. It most frequently occurs in women in their late 40's, but recently, its attack in young age groups shows a tendency of an increase. If it has developed, it can be difficult to cure completely, but if it is diagnosed early, it can be completely cured by the modern medicine. Also, it is known that cervical precancer lesions occur before progression to cervical cancer, and thus, it is important to diagnose cervical cancer at the early stage.

Although the cause of the development of cervical cancer is not yet completely explored, but HPV is being noticed as the most important cause factor. Some of HPV infections are progressed to cervical cancer via precursor lesions such as high grade squamous intraepithelial lesion (HSIL), Carcinoma in situ (CIS), and this process is known to occur over a significant period of time. Thus, the detection of HPV infection with PAP smear, colposcopy, or cervicography, etc., which is known for early diagnosis method of uterine cancer will greatly help early diagnosis of cervical cancer.

Methods for detecting HPV infection and genotype can be broadly divided into an in situ detection method for HPV DNA, and a method using HPV DNA amplification. Examples of the in situ detection method for HPV DNA include liquid hybridization (hybrid capture by digene diagnostics, Silver Spring, Md.), Southern blot and dot blot using HPV type-specific probes, and filter in situ hybridization (FISH).

Examples of the method using HPV DNA amplification include type-specific PCR, and general primer PCR. The genotypes of HPV DNA amplified with a general primer set can be detected by various methods, including dot blot hybridization, microtiter plate hybridization and line probe assay. The line probe assay is a method for detecting about 20 genotypes using oligonucleotide probes immobilized on a nitrocellulose membrane, but has several problems in view of probe sensitivity and data analysis.

Furthermore, a commercial hybrid capture kit can detect HPV DNA without PCR by easily isolating HPV DNA from a clinical sample. However, this kit makes it possible to only determine whether the corresponding HPV DNA belongs to high-risk group or to low-risk group, and it is impossible for this kit to determine an accurate genotype. Thus, there is a problem in that noteworthy HPV genotypes (HPV 16 and 18) among the high-risk groups, i.e., genotypes having a very high correlation with the generation of cancer, cannot be distinguished from other high-risk groups (medium risk groups). Moreover, due to the use of RNA probes, this method has other problems in that stability is low and contamination possibility cannot be excluded.

In addition, there is another method for detecting HPV DNA, in which a chip on which about 50 bp single-stranded oligonucleotide derived from various HPV genotypes is integrated is brought into contact with a fluorescence-labeled DNA sample containing a base sequence specific to HPV genotypes, and then, HPV infections are determined depending on whether HPV DNA hybridization occurs or not. However, this method has a shortcoming that a process after preparing a chip is complicated as compared to a method using a DNA chip on which double-stranded DNA is integrated. Another shortcoming is that it is not easy for the DNA sample to access to the probe on the chip depending on the coating uniformity of a glass slide surface, so that the signal intensity after hybridization has no consistency.

In an attempt to solve the above-mentioned problems occurring in the prior art, the present inventors constructed a DNA chip by cloning a probe comprising a linker coupled to both ends of about 60 bp target oligonucleotide, into a vector and culturing host cells transformed with the vector, to recover the probe, and integrating the recovered double-helical probe on a substrate. Then, the inventors have found that such a DNA chip showed good signal intensity after hybridization, thereby completing the present invention.

DISCLOSURE OF INVENTION

Therefore, a main object of the present invention is to provide a DNA chip which shows excellent signal intensity after hybridization, without being influenced by the coating uniformity of a glass slide surface, as well as a producing method thereof.

Another object of the present invention is to provide a DNA chip for HPV diagnosis which shows excellent signal intensity after hybridization, without being influenced by the coating uniformity of a glass slide surface, as well as a producing method thereof.

Still another object of the present invention is to provide a method for diagnosing the presence or genotype of HPV using the above DNA chip for HPV diagnosis.

To achieve the above objects, in one aspect, the present invention provides a method for producing a DNA chip, the method comprising the steps of: (a) cloning a probe, where a linker is coupled to one or both ends of an oligonucleotide to be integrated on a slide, into a vector; (b) transforming host cells with the vector; (c) culturing the transformed host cells, to recover the probe where the linker is coupled to one or both ends of the oligonucleotide; and (d) integrating the obtained double-helical probe on a slide.

Examples of the vector, which can be used in the inventive method for producing the DNA chip, include a plasmid vector, a bacteriophage vector, a cosmid vector, an yeast artificial chromosome (YAC) vector. For the purpose of the present invention, the plasmid vector is preferably used. A typical plasmid vector which can be used for this purpose contains the following: (a) a replication origin by which replication occurs efficiently such that several hundred plasmid vectors per host cell are created; (b) an antibiotic-resistant gene by which host cells transformed with the plasmid vector can be selected; and (c) restriction enzyme cutting sites into which foreign DNA fragments can be inserted. Even if suitable restriction enzyme cutting sites are not present in the vector, the use of a conventional synthetic oligonucleotide adaptor or linker enables the easy ligation between the vector and the foreign DNA fragments.

Various vectors, including a T-vector used in the present invention, have a multicloning site (MCS) containing several restriction enzyme cutting sites, which is located within a lacZ gene. Since MCS does not destroy the reading frame of the lacZ gene, the expression of the lacZ gene in suitable host cells occurs to synthesize β-galactosidase enzyme which has biological activity. When such host cells are cultured in a medium containing the colorless chemical substance X-gal, X-gal is decomposed by this enzyme to form an insoluble blue substance. Thus, host cell colonies transformed with a plasmid vector containing MCS having no foreign DNA inserted therein have blue color. On the contrary, when foreign DNA is inserted into MCS, the lacZ reading frame of the plasmid vector is broken such that β-galactosidase is not synthesized, and thus, colorless host cell colonies are formed. In the inventive method for producing the DNA chip, this vector is very useful since it confirms whether DNA to be integrated on a slide was normally cloned into the vector.

After ligation, the vector should be transformed into suitable host cells. In the inventive method for producing the DNA chip, the host cells are preferably prokaryotic cells. Preferred examples of the prokaryotic host cells include *E. coli* DH5a, *E. coli* JM101, *E. coli* K12, *E. coli* W3110, *E. coli* X1776, *E. coli* XL-1Blue (Stratagene, Co.) and *E. coli* B. However, other *E. coli* strains, such as FMB101, NM522, NM538 and NM539, and other prokaryotic species and genera, may also be used. In addition to the *E. coli* strains as described above, bacilli, such as *Bacillus subtilis*, other intestinal bacteria, such as *Salmonella typhimurium* and *Serratia marcescens*, and various *Pseudomonas* species, may be used as the host cells.

The transformation of the prokaryotic cells can be easily achieved by the calcium chloride method. Alternatively, electroporation may be used to transform such cells (Neumann et al, *EMBO J.,* 1:841, 1982).

Cells transformed with a vector into which DNA to be integrated on a slide were normally inserted are selected, and cultured in a medium, from which the vector is then isolated. The vector can be easily isolated by any method known in the art. When PCR is performed using the isolated vector as a template and primers specific to sites containing DNA to be integrated on a slide, DNA to be integrated on a slide can be produced at large amounts.

In the present invention, the oligonucleotide is preferably 40-80 bp in length, and the linker is preferably 30-300 bp in length, and is a part of the base sequence of a T-vector. More preferably, the linker is coupled to both ends of the oligonucleotide and is 30-150 bp in length.

In the present invention, the oligonucleotide to be integrated on a slide is preferably an oligonucleotide having a base sequence specific to HPV genotypes. The base sequence specific to the HPV genotypes is preferably a 60 bp base sequence (nucleotides 6796-6855 of HPV genomic DNA) located within a 150 bp base sequence (nucleotides 6765-6915 of HPV genomic DNA) in a HPV L1 gene.

The inventive method for producing the DNA chip provides the following advantages: (1) an oligonucleotide to be integrated on a slide can be amplified by the culture of host cells in addition to PCR; (2) when the oligonucleotide to be integrated on a slide is produced by PCR, a sequence, present in the vector can be used as primers, so that the oligonucleotide can be easily amplified regardless of its sequence; (3) the storage of the oligonucleotide to be integrated on a slide becomes possible by the storage of host cells; (4) The production of a DNA chip in a subsequent stage can be achieved in a simple manner by isolating the vector from the stored host cells, PCR-amplifying an oligonucleotide to be integrated on a slide using the vector, and integrating the PCR products on a slide; and (5) when the primer mentioned in the part (2) is chemically modified (e.g., an amine group is bound to the 5' end) and PCR is performed with the modified primer, the PCR-amplified DNA can be integrated also on a slide for single-stranded oligonucleotides, thus indicating that a slide has a wide range of selection.

In another aspect, the present invention provides a DNA chip for HPV diagnosis, which is produced by the inventive method as described above, and in which a probe comprising about 30-150 bp of a linker coupled to both ends of about 60 bp of an oligonucleotide containing a base sequence specific to HPV genotypes is integrated on a slide.

A probe suitable for the DNA chip is a double-helical DNA containing a base sequence specific to HPV genotypes. By the results of base sequence analysis of HPV, a 150 bp base sequence (corresponding to nucleotides 6765-6915 of HPV genomic DNA; and hereinafter, referred to as 6765-6915) located within an HPV L1 gene is known as a base sequence specific to HPV genotypes, and widely used in HPV typing. Particularly, the 150 bp base sequence (6765-6915) located within the HPV L1 gene is useful in that it can be PCR-amplified with two concensus primers (G5+/Gp6+) in almost all genotypes. In the present invention, a 60 bp base sequence (corresponding to nucleotides 6796-6855 of HPV genomic DNA; and hereinafter, 6796-6855), which is located within the 150 bp base sequence (6765-6915) and specific to HPV genotypes, is preferably selected as a sequence to be included in a probe.

The inventive DNA chip for HPV diagnosis preferably comprises a PCR control, and a positive or negative control, as well as a double-helical DNA probe containing the 60 bp base sequence (6796-6855), which is located within the 150 bp base sequences (6765-6915) of HPV L1 gene and specific to an HPV genotype.

The inventive DNA chip for HPV diagnosis contains a PCR control. The application of such a DNA chip generally includes a process of performing PCR using a genomic DNA isolated from clinical samples, as a template, and primers capable of amplifying the desired base sequence. In this PCR process, when the PCR reaction solution contains primers capable of amplifying the PCR control, both the desired base sequence and the PCR control are amplified. Thus, if the PCR products from PCR that was normally performed are in contact with the DNA chip, hybridization will occur also in the PCR control. In other words, the amplification of the PCR control confirms that PCR was normally performed.

The inventive DNA chip for HPV diagnosis preferably contains a positive control. As used herein, the term "positive control" refers to a 150 bp base sequence (6765-6915) mixture located within an HPV L1 gene which can be amplified with a primer mixture. The primer mixture contains GP5+/GP6+ primer and an additional primer required to amplify the 150 bp base sequence (6765-6915) within the HPV L1 gene which cannot be amplified with GP5+/GP6+ primer. If PCR is performed using such a primer mixture, the 150 bp base sequence (6765-6915) located within the HPV L1 gene, derived from all the known HPV genotypes, will be obtained, and the mixture of the 150 bp base sequences is the very positive control. Thus, if HPV is present in a clinical sample, hybridization will occur not only in a probe containing a base sequence specific to HPV genotypes but also in the positive control. Even if the inventive DNA chip contains no probe corresponding to a certain genotype, it can detect the presence of HPV in a clinical sample, since hybridization occurs also in the positive control. The use of such results can help a secondary diagnostic test, such as the detection of genotypes.

The double-helical DNA probe containing the base sequence specific to HPV genotypes, the PCR control, and the positive or negative control, can be attached to a slide by a pin microarray or inkjet method, thus producing a DNA chip. The pin microarray method is developed by Patrick O. Brown, biochemistry professor at Stanford University, and currently often used. Also, it is a method by which probes can be aligned at desired locations by loading a given amount of a previously synthesized DNA sample solution into the tip of a pin and then bringing the pin tip into contact with a slide. The inkjet method is almost similar to the pin microarray method, except that DNA is sprayed onto a solid substrate by a device, such as one used in an inkjet printer, in place of a pin, without contact with a slide. Methods known to be used for the spray of DNA till now are three methods, including thermal, solenoid and piezoelectric methods.

In still another aspect, the present invention provides a method for preparing a DNA sample, in which a genomic DNA is isolated from a clinical sample to be diagnosed for HPV infection, and PCR is performed using the isolated DNA, as a template, and using primers corresponding to a sequence specific to HPV genotypes, the method being characterized by that a mixture containing primers of SEQ ID NO: 57 to SEQ ID NO: 60 is used as the primers:

```
                                        SEQ ID NO: 57
(GP5+): 5'-TTTGTTACTGTGGTAGATACTAC-3';

SEQ ID NO: 58
(GP6+): 5'-GAAAAATAAACTGTAAATCATATTC-3';

SEQ ID NO: 59
(GP5-M): 5'-TTTNTNACHGTDGTDGAYACHAC-3';
and
                                        SEQ ID NO: 60
(GP6-M): 5'-GAAAHATAAAYTGYAVDTCAWAYTC-3'.
```

Wherein, N denotes A, C, T or G; H denotes A, C or T; D denotes A, G or T; Y denotes C or T; W denotes A or T; R denotes A or G; and V denotes A, C or G.

In yet another aspect, the present invention provides a method for diagnosing the presence or genotype of HPV, the method comprising the step of: hybridizing the DNA sample prepared by the above method with said DNA chip for HPV diagnosis.

In order to diagnose HPV with a DNA chip, a DNA sample capable of contacting with the DNA chip must be first prepared from a clinical sample. As used herein, the term "clinical sample" refers to populations, tissues or cells to be diagnosed for HPV infection. Also, the term "DNA sample" refers to PCR products obtained by isolating a genomic DNA from a clinical sample and performing PCR using the desired DNA fragment as a template. In the present invention, the desired DNA fragment refers to a 150 bp base sequence (6765-6915) located within an L1 gene, and it can be easily amplified en bloc using the primer mixture of the present invention, regardless of HPV genotypes. In addition, fluorescent substances are added to the PCR reaction solution, so that the desired fragment to be amplified and the control groups can be labeled with the fluorescent substances. Any fluorescent substances known in the art may be used in the present invention, and preferably, the use of fluorescence-linked nucleotides facilitates the labeling.

The existing DNA chip for HPV diagnosis contains a single-stranded probe, whereas the inventive DNA chip is characterized by that it contains a double-helical probe. If a probe is single-stranded, a fluorescence-labeled single-stranded DNA is hybridized with the single-stranded probe. If a probe is double-helical, double-helical DNA consisting of fluorescence-labeled single strands is hybridized with the double-helical probe. Thus, when hybridization occurs, the signal intensity of the latter is higher than that of the former, because the latter contains more fluorescent substances than that of the former.

Furthermore, the inventive DNA chip is characterized by that it is produced by a method comprising: cloning a probe where a linker is coupled to both ends of a target oligonucleotide into a vector, easily recovering the probe by culturing host cells transformed with the vector, thereby integrating the recovered double-helical probe on a substrate. Thus, the inventive DNA chip makes it possible to solve the shortcoming of the prior art that the signal intensity after hybridization has no consistency since it is not easy for a DNA sample to access to a probe on a chip depending on the coating uniformity of a glass slide surface.

BRIEF DESCRIPTIONS OF DRAWINGS

Figure 6:
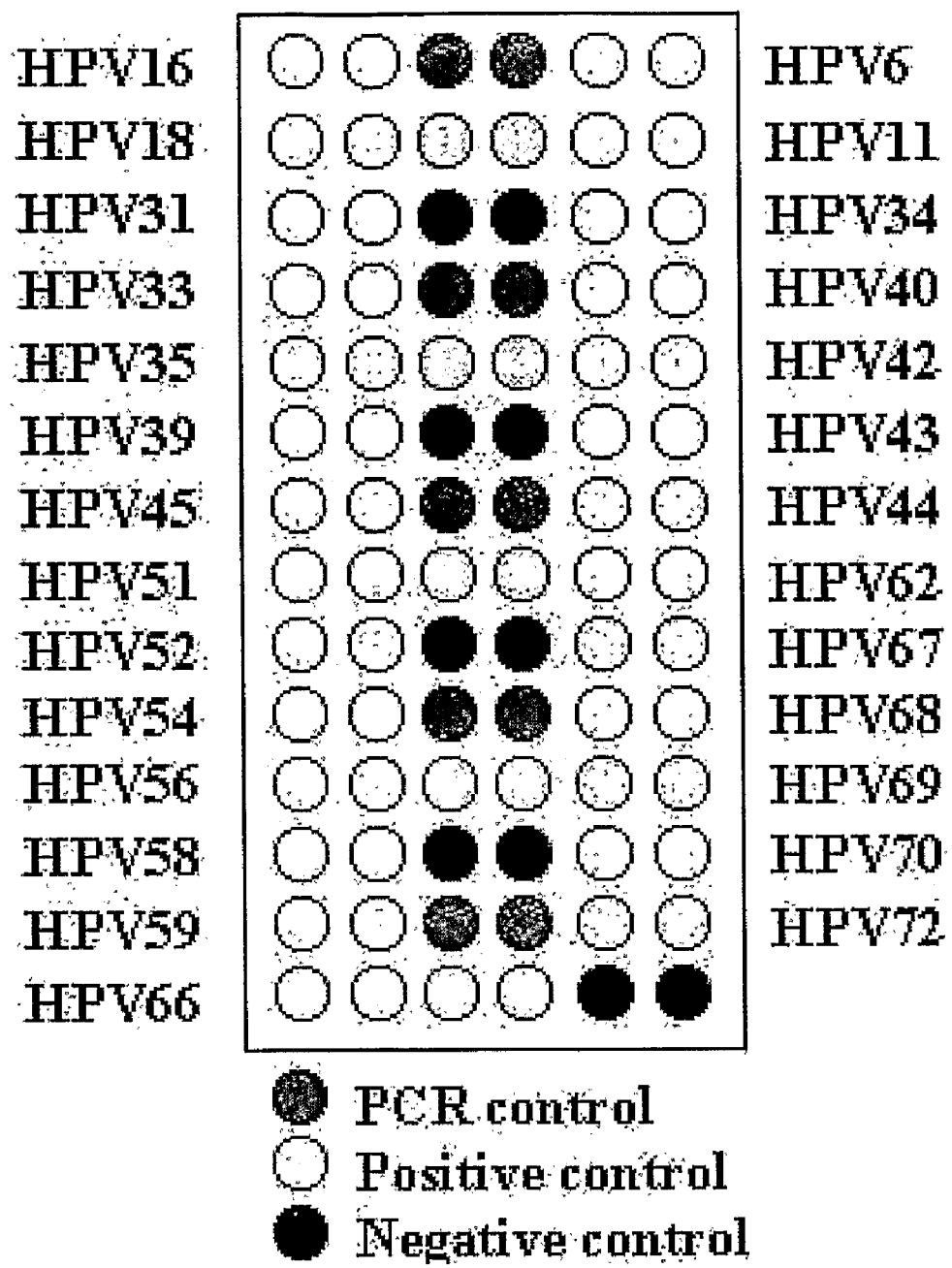

FIG. 6 schematically shows a DNA chip for HPV diagnosis (Left panel: HPV probes belonging to high-risk groups; and Right panel: HPV probes belonging to low-risk groups).

Figure 7:
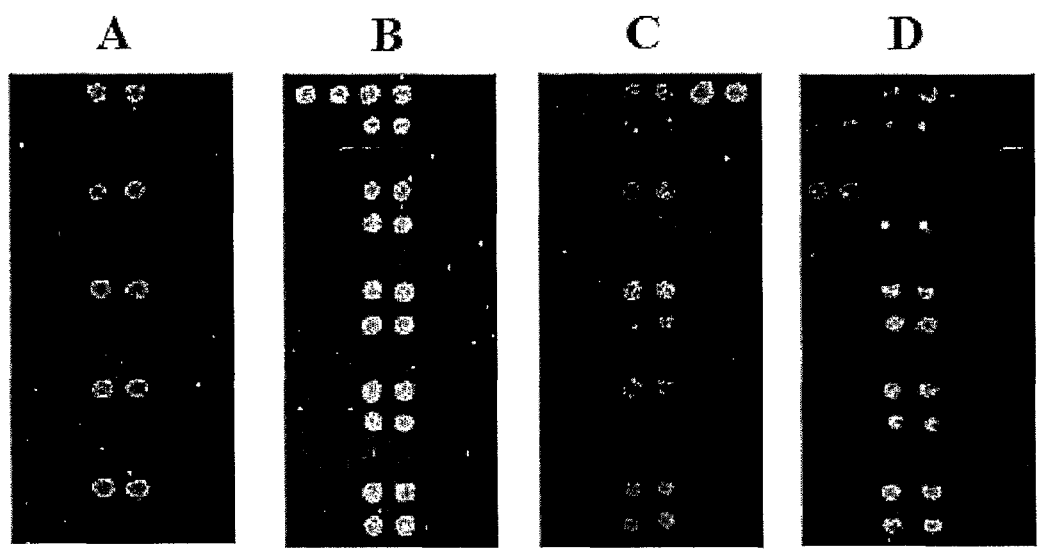

FIG. 7 shows the results of a hybridization test on whether a DNA chip for HPV diagnosis is suitable as a tool for the diagnosis of the presence or genotype of HPV (A: clinical sample uninfected with HPV; B: clinical sample infected with HPV 6; C: clinical sample infected with HPV 16; and D: clinical sample infected with HPV 16 and 33).

DETAILED DESCRIPTION OF THE INVENTION

The present invention will hereinafter be described in further detail by examples. It will however be obvious to a person skilled in the art that the present invention is not limited to or by the examples.

EXAMPLE 1

Figure 1:
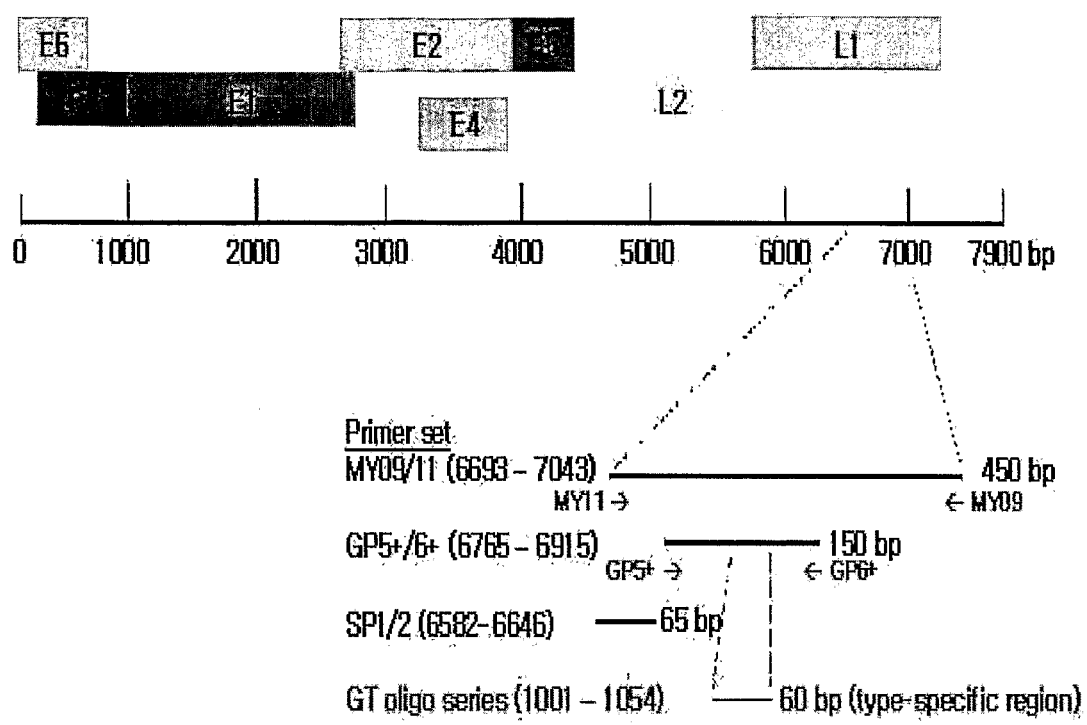
FIG. 1 is a genetic map of HPV genotype 16.

Production of Probe Containing 60 bp Base Sequence (6796-6855) Specific to HPV Genotypes As a base sequence specific to HPV genotypes, a 150 bp base sequence (6765-6915) located within an L1 gene is known. In the present invention, a 60 bp base sequence (6796-6855) located within the 150 bp base sequence and specific to HPV genotypes, was synthesized (FIG. 1).

Each 1 μg of the synthesized 60 bp single-stranded oligonucleotides was denatured for 10 minutes at 94° C. and left as it is for 30 minutes at room temperature to induce spontaneous annealing, thus preparing a 60 bp double-helical DNA. To clone the 60 bp DNA into a T-vector, a reaction for adding adenine to both ends of the 60 bp DNA was performed using a PCR machine. For this purpose, 1 μg of 60 bp double-helical DNA, 2.5 mM of dATP, 5 μl of 10×PCR buffer (Solgent Co.) and 2.5 units of Taq DNA polymerase were mixed to a final volume of 50 μl, and then the mixture was allowed to react at 72° C. for 2 hours (FIG. 2).

Figure 2:
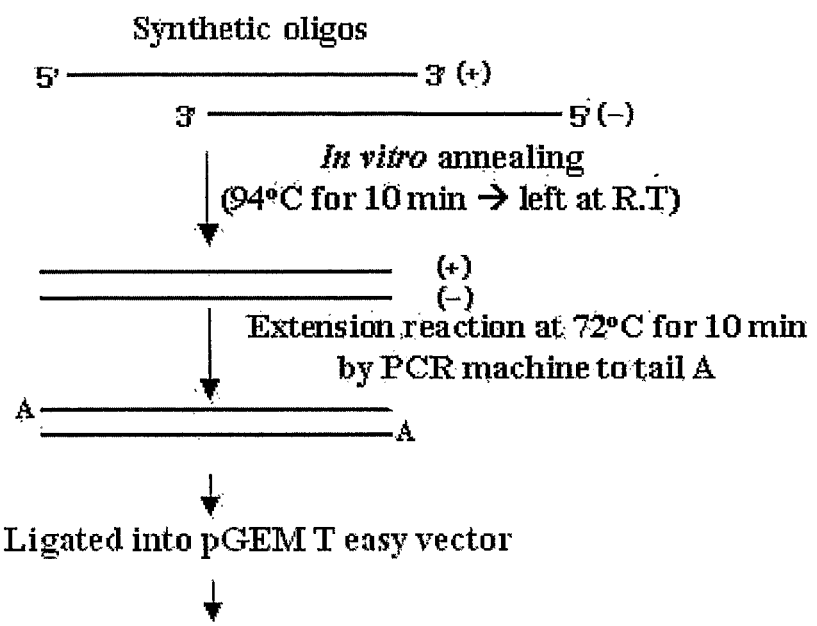
FIG. 2 shows a producing method of a probe containing a base sequence specific to HPV genotypes.
Figure 3:
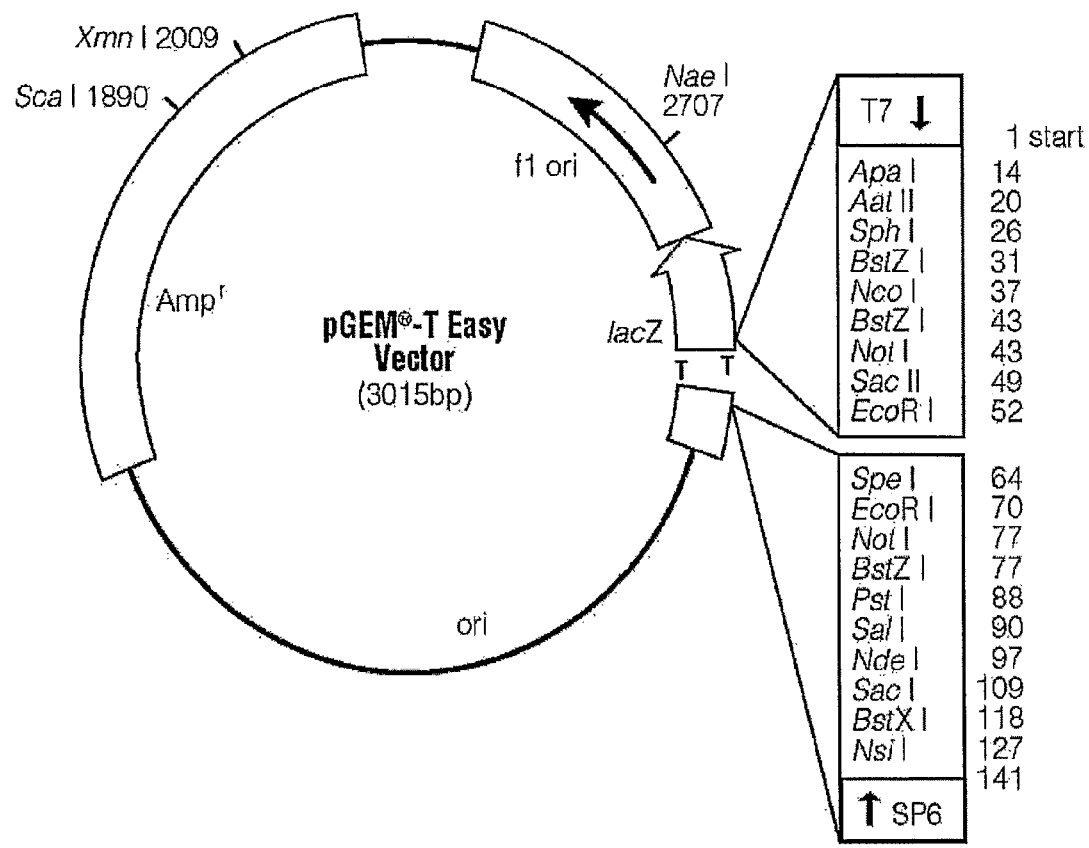
FIG. 3 is a genetic map of a pGEM T Easy vector.
Figure 4:
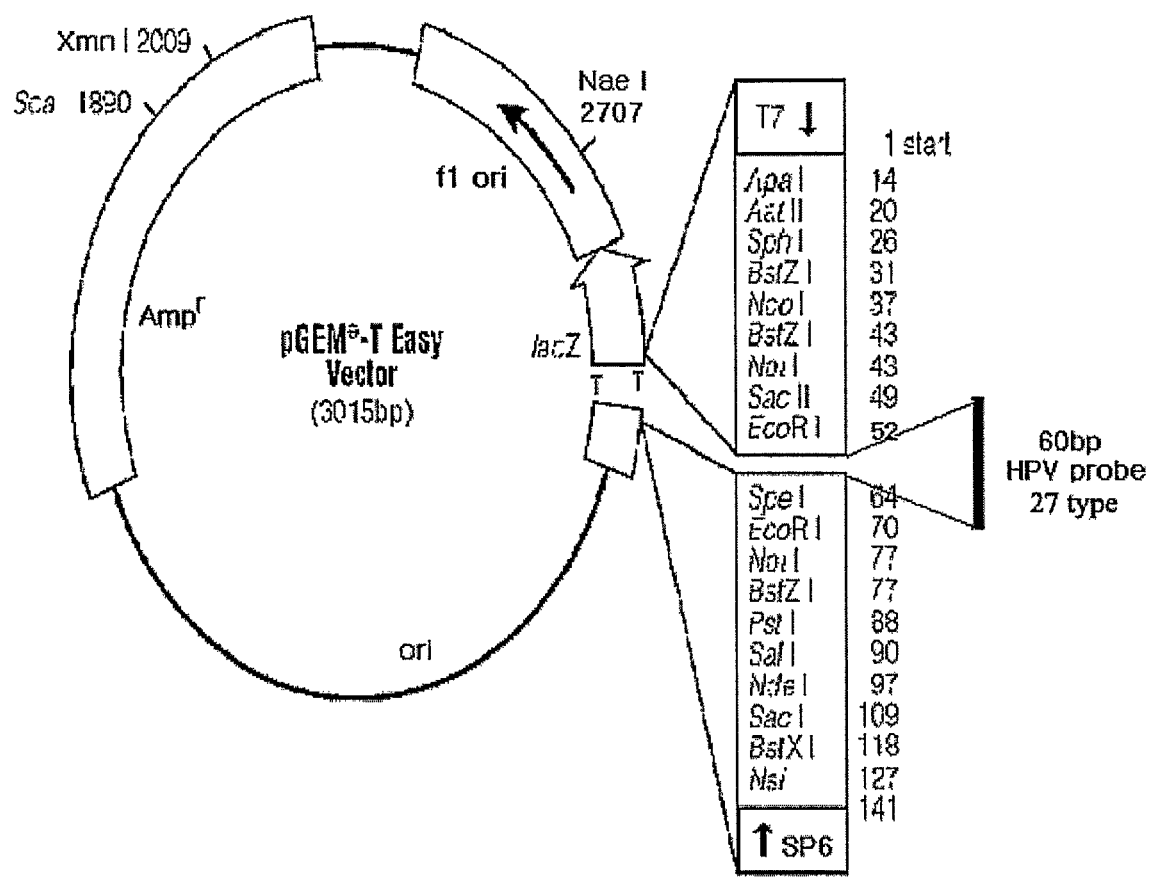
FIG. 4 is a genetic map of a pGEM T Easy vector into which a sequence specific to HPV genotypes was cloned.

100 ng of the resulting DNA was mixed well with 40 ng of a T-vector (pGEM T Easy vector), and the DNA was ligated into the T-T site of the T-vector (FIG. 2 and FIG. 3). The ligation was performed to a volume of 20 μl at 16° C. for 8 hours according to the manufacturer's instruction. 10 μl of the ligation reaction mixture was transformed into a DH5α E. coli strain, thus securing 27 plasmid DNAs cloned with the DNA containing a sequence specific to HPV genotypes (FIG. 4).

The HPV probe clone name, base sequence name and base sequence of such 27 plasmid DNAs are as follows:

pHPV6

(SEQ ID NO: 1)
GT1001: 5'-CCA ACA TGA CAT TAT GTG CAT CCG TAA CTA CAT CTT CCA CAT ACA CCA ATT CTG ATT ATA-3'

(SEQ ID NO: 2)
GT1002: 5'-TAT AAT CAG AAT TGG TGT ATG TGG AAG ATG GAT TTA CGG ATG CAC ATA ATG TCA TGT TGG-3' pHPV11

(SEQ ID NO: 3)
GT1003: 5'-TAT GAC ACT ATG TGC ATC TGT GTC TAA ATC TGC TAC ATA CAC TAA TTC AGA TTA TAA GGA-3'

(SEQ ID NO: 4)
GT1004: 5'-TCC TTA TAA TCT GAA TTA GTG TAT GTA GCA GAT TTA GAC ACA GAT GCACAT AGT GTC ATA-3' pHPV16

(SEQ ID NO: 5)
GT1005: 5'-ACG CAG TAC AAA TAT GTC ATT ATG TGC TGC CAT ATC TAC TTC AGA AAC TAC ATA TAA AAA-3'

(SEQ ID NO: 6)
GT1006: 5'-TTT TTA TAT GTA GTT TCT GAA GTA GAT ATG GCA GCA CAT AAT GAC ATA TTT GTA CTH CGT-3' pHPV18

(SEQ ID NO: 7)
GT1007: 5'-GAA TTT AAC AAT ATG TGC TTC TAC ACA GTC TCC TGT ACC TGG GCA ATA TGA TGC TAC CAA-3'

(SEQ ID NO: 8)
GT1008: 5'-TTG GTA GCA TCA TAT TGC CCA GGT ACA GGA GAC TGT GTA GAA GCA CAT ATT GTT AAA TTG-3' pHPV31

(SEQ ID NO: 9)
GT1009: 5'-TAG TAC CAA TAT GTC TGT TTG TGC TGC AAT TGC AAA CAG TGA TAC TAC ATT TAA AAG TAG-3'

(SEQ ID NO: 10)
GT1010: 5'-CTA CTT TTA AAT GTA GTA TCA CTG TTT GCA ATT GCA GCA CAA ACA GAC ATA TTG GTA CTA-3' pHPV33

(SEQ ID NO: 11)
GT1011: 5'-CAG TAC TAA TAT GAC TTT ATG CAC ACA AGT AAC TAG TGA CAG TAC ATA TAA AAA TGA AAA-3'

(SEQ ID NO: 12)
GT1012: 5'-TTT TCA TTT TTA TAT GTA CTG TCA CTA GTT ACT TGT GTG CAT AAA GTC ATA TTA GTA CTG-3' pHPV34

(SEQ ID NO: 13)
GT1013: 5'-TTC AGT TTG TGT AGG TAC ACA ATC CAC AAG TAC AAC TGC ACC ATA TGC AAA CAG TAA TTT-3'

(SEQ ID NO: 14)
GT1014: 5'-AAA TTA CTG TTT GCA TAT GGT GCA GTT GTA CTT GTG GAT TGT GTA CCT ACA CAA ACT GAA-3' pHPV35

(SEQ ID NO: 15)
GT1015: 5'-CCG TAG TAC AAA TAT GTC TGT GTG TTC TGC TGT GTC TTC TAG TGA CAG TAC ATA AAA-3'

(SEQ ID NO: 16)
GT1016: 5'-TTT TTA TAT GTA CTG TCA CTA GAA GAC ACA GCA GAA CAC ACA GAC ATA TTT GTA CTA CGG-3' pHPV39

(SEQ ID NO: 17)
GT1017: 5'-ACC AAC TTT ACA TTA TCT ACC TCT ATA GAG TCT TCC ATA CCT TCT ACA TAT GAT CCT TCT-3'

(SEQ ID NO: 18)
GT1018: 5'-AGA AGG ATC ATA TGT AGA AGG TAT GGA AGA CTC TAT AGA GGT AGA TAA TGT AAA GTT GGT-3' pHPV40

(SEQ ID NO: 19)
GT1019: 5'-AAT TTA ACC TTA TGT GCT GCC ACA CAG TCC CCC ACA CCA ACC CCA TAT AAT AAC AGT AAT-3'

(SEQ ID NO: 20)
GT1020: 5'-ATT ACT GTT ATT ATA TGG GGT TGG TGT GGG GGA CTG TGT GGC AGC ACA TAA GGT TAA ATT-3' pHPV42

(SEQ ID NO: 21)
GT1021: 5'-TGA CTT TGT GTG CCA CTG CAA CAT CTG TGT ATA CAT ATA CAG CTG CTA TTT TAG GAA AT-3'

(SEQ ID NO: 22)
GT1022: 5'-ATT CCT AAA ATA GCA GCT GTA TAT GTAT CAC CAG ATGTTG CAG TGG CAC ACA AAG TCA-3' pHPV43

(SEQ ID NO: 23)
GT1023: 5'-TTG ACG TTA TGT GCC TCT ACT GAC CCT ACT GTG CCC AGT ACA TAT GAC AAT GCA AAG TTT-3'

-continued

```
                                        (SEQ ID NO: 24)
GT1024: 5'-AAA CTT TGA ATT GTC ATA TGT ACT GGG CAC
AGT AGG GTC AGT AGA GGC ACA TAA CGT CAA-3' pHPV44
                                        (SEQ ID NO: 25)
GT1025: 5'-ATG ACA ATA TGT GCT GCC ACT ACA CAG TCC
CCT CCG TCT ACA TAT ACT AGT GAA CAA TAT-3'

(SEQ ID NO: 26)
GT1026: 5'-ATA TTG TTC ACT AGT ATA TGT AGA CGG AGG
GGA CTG TGT AGT GGC AGC ACA TAT TGT CAT-3' pHPV45
                                        (SEQ ID NO: 27)
GT1027: 5'-ACA TTA TGT GCC TCT ACA CAA AAT CCT GTG
CCA AGT ACA TAT GAC CCT ACT AAG TTT AAG-3'

(SEQ ID NO: 28)
GT1028: 5'-CTT AAA CTT AGT AGG GTC ATA TGT ACT TGG
CAC AGG ATT TTG TGT AGA GGC ACA TAA TGT-3' pHPV51
                                        (SEQ ID NO: 29)
GT1029: 5'-ACA AAT TTA ACT ATT AGC ACT GCC ACT GCT
GCG GTT TCC CCA ACA TTT ACT CCA AGT AAC-3'

(SEQ ID NO: 30)
GT1030: 5'-GTT ACT TGG AGT AAA TGT TGG GGA AAC CGC
AGC AGT GGC AGT GCT AAT AGT TAA ATT TGT-3' pHPV52
                                        (SEQ ID NO: 31)
GT1031: 5'-TAA CAT GAC TTT ATG TGC TGA GGT TAA AAA
GGA AAG CAC ATA TAA AAA TGA AAA TTT TAA-3'

(SEQ ID NO: 32)
GT1032: 5'-TTA AAA TTT TCA TTT TTA TAT GTG CTT TCC
TTT TTA ACC TGA GCA CAT AAA GTC ATG TTA-3' pHPV54
                                        (SEQ ID NO: 33)
GT1033: 5'-CCT AAC ATT GTG TGC TAC AGC ATC CAC GCA
GGA TAG CTT AAA TAA TTC TGA CTT TAG GGA-3'

(SEQ ID NO: 34)
GT1034: 5'-TCC CTA AAG TCA GAA TTA TTA AAG CTA TCC
TGC GTG GAT GCT GTA GCA CAC AAT GTT AGG-3' pHPV56
                                        (SEQ ID NO: 35)
GT1035: 5'-CTA ACA TGA CTA TTA GTA CTG CTA CAG AAC
AGT AAA GTA AAT ATG ATG CAC GAA AAA TTA-3'

(SEQ ID NO: 36)
GT1036: 5'-TAA TTT TTC GTG CAT CAT ATT TAC TTA TCT
GTT CTG TAG CAG TAC TAA TAG TCA TGT TAG-3' pHPV58
                                        (SEQ ID NO: 37)
GT1037: 5'-TAG CAC TAA TAT GAC ATT ATG CAC TGA AGT
AAC TAA GGA AGG TAC ATA TAA AAA TGA TAA-3'

(SEQ ID NO: 38)
GT1038: 5'-TTA TCA TTT TTA TAT GTA CCT TCC TTA GTT
ACT TCA GTG CAT AAT GTC ATA TTA GTG CTA-3' pHPV59
                                        (SEQ ID NO: 39)
GT1039: 5'-CTT TCT GTG TGT GCT CTA CTA CTC TCT ATT
CCT AAT GTA TAC ACA CCT ACC AGT TTT AAA-3'

(SEQ ID NO: 40)
GT1040: 5'-TTT AAA ACT GGT AGG TGT GTA TAC ATT AGG
AAT AGA GAG TAG TAG AGC ACA CAC AGA AAG-3' pHPV62
                                        (SEQ ID NO: 41)
GT1041: 5'-TTT GTA CCG CCT CCA CTG CTG CAG CAG AAT
ACA CGG CTA CCA ACT TTA GGG AAT TTT TGC-3'

(SEQ ID NO: 42)
GT1042: 5'-GCA AAA ATT CCC TAA AGT TGG TAG CCG TGT
ATT CTG CTG CAG CAG TGG AGG CGG TAC AAA-3' pHPV66
                                        (SEQ ID NO: 43)
GT1043: 5'-GCA GCT AAA AGC ACA TTA ACT AAA TAT GAT
GCC CGT GAA ATC AAT CAA TAC CTT CGC CAT-3'

(SEQ ID NO: 44)
GT1044: 5'-ATG GCG AAG GTA TTG ATT GAT TTC ACG GGC
ATC ATA TTT AGT TAA TGT GCT TTT AGC TGC-3' pHPV67
                                        (SEQ ID NO: 45)
GT1045: 5'-TAT ATT CTG AGG GAA AAT CAG AGG CTA CAT
ACA AAA ATG AAA ACT TTA GGA ATA CCC TTA-3'

(SEQ ID NO: 46)
GT1046: 5'-TAA GGT ATT CCT TAA AGT TTT CAT TTT TGT
ATG TAG CCT CTG ATT TTC CCT CAG AAT ATA-3' pHPV68
                                        (SEQ ID NO: 47)
GT1047: 5'-TGT CTA CTA CTA CTG AAT CAG CTG TAC CAA
ATA TTT ATG ATC CTA ATA ATT TAG GAA T-3'

(SEQ ID NO: 48)
GT1048: 5'-ATT CCT AAA TTA TTA GGA TCA TAA ATA TAT
TTG GTA CAG CTG ATT CAG TAG TAG TAG ACA-3' pHPV69
                                        (SEQ ID NO: 49)
GT1049: 5'-ACT GTA TCT GCA CAA TCT GCA TCT GCC ACT
TTT AAA CCA TCA GAT TAT AAG CAG TTT ATA-3'

(SEQ ID NO: 50)
GT1050: 5'-TAT AAA CTG CTT ATA ATC TGA TGG TTT AAA
AGT TGC AGA TGC AGA TTG TGC AGA TAC AGT-3' pHPV70
                                        (SEQ ID NO: 51)
GT1051: 5'-GCC TGC ACC GAA ACG GCC ATA CCT GCT GTA
TAT AGC CCT ACA AAG TTT AAG AAA TAT ACT-3'

(SEQ ID NO: 52)
GT1052: 5'-AGT ATA TTC TTA AAA CTT TGT AGG GCT ATA
TAC AGC AGG TAT GGC CGT TTC GGT GCA GGC-3' pHPV72
                                        (SEQ ID NO: 53)
GT1053: 5'-ACT GCC ACA GCG TCC TCT GTA TCA GAA TAT
ACA GCT TCT AAT TTT CGT GAG TAT CTT CGC-3'

(SEQ ID NO: 54)
GT1054: 5'-GCG AAG ATA CTC ACG AAA ATT AGA AGC TGT
ATA TTC TGA TAC AGA GGA CGC TGT GGC AGT-3'
```

EXAMPLE 2

Production of DNA Chip for HPV Diagnosis

The T-vector containing a base sequence specific to HPV genotypes was isolated from the transformed *E. coli*. PCR was performed using primer T7 and primer SP6, to amplify 240 bp DNA fragments containing a 60 bp base sequence (6796-6855) specific to HPV genotypes and parts of the base sequence of the T-vector (base sequences pSP6 to pT7 of pGEM T Easy vector). In the PCR reaction, 20 pmol of primers, 2.5 mM of dNTP mixture, 100 ng of plasmid DNA, 5 µl of 10× PCR buffer (Solgent Co.) and 2.5 units of Taq DNA polymerase were mixed to a final volume of 50 µl, and the mixture was subjected to 34 PCR cycles, each cycle consisting of denaturation for 10 minutes at 94° C.; denaturation for 1 minute at 94° C.; annealing for 45 seconds at 55° C.; and extension for 45 seconds at 72° C. A final extension of 10 minutes at 72° C. was followed.

Figure 5:
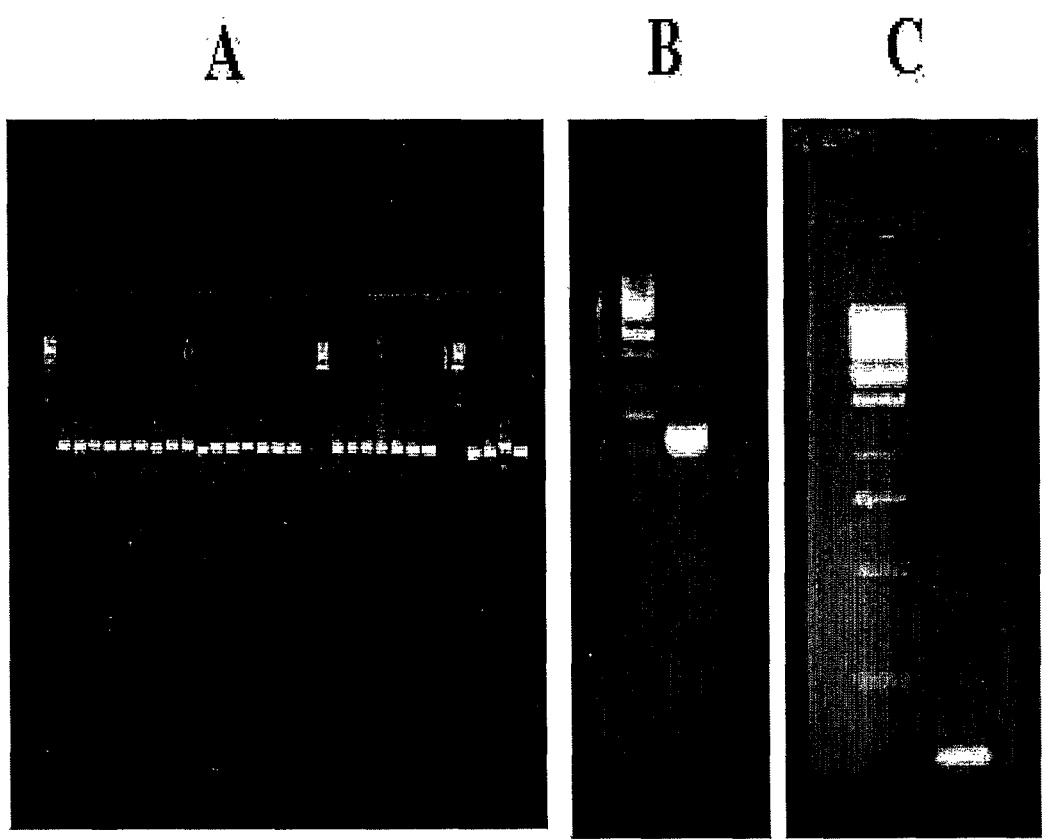
FIG. 5 shows the results of agarose gel electrophoresis of an HPV probe amplified by PCR, a PCR control, and a positive control (A: 27 probes (240 bp) containing a base sequence specific to HPV genotypes; B: PCR control GADPH (600 bp); and C: positive control).

The amplified DNA fragments were purified with a QuiaQuick PCR purification kit(Qiagen), and electrophoresed on 2% agarose gel to determine the PCR products. The base sequence of HPV DNA in each plasmid was analyzed to confirm the HPV clones (FIG. 5).

The PCR products were dried, dissolved in 20 µl of 50% DMSO solution and integrated on a Corning GAPS slide for DNA chips, thus producing a DNA chip. The resulting DNA chip was cross-linked by irradiation with UV of 300 mJ, and then stored on a drying rack at room temperature (FIG. 6).

EXAMPLE 3

Preparation of DNA Sample and Use of DNA Chip for HPV Diagnosis

A test was performed to determine whether the inventive DNA chip is suitable as a kit for the diagnosis of the presence or genotype of HPV. Genomic DNAs were isolated from HPV-uninfected clinical samples and HPV-infected clinical samples (infected with HPV 6, HPV 16, and HPV 16 and 33, respectively), and subjected to PCR. The PCR reaction solution contained: (1) PCR control primers and (2) a primer mixture.

```
(1) PCR control primers (primers for GAPDH
amplification):
                                    (SEQ ID NO: 55)
GAPDH F: 5'-TCA ACG GAT TTG GTC GTA TT-3'

(SEQ ID NO: 56)
GAPDH R: 5'-TAG AGG CAG GGA TGA TGT TC-3'

(2) primer mixture:
                                    (SEQ ID NO: 57)
GP5+: 5'-TTT GTT ACT GTG GTA GAT ACT AC-3'

(SEQ ID NO: 58)
GP6+: 5'-GAA AAA TAA ACT GTA AAT CAT ATT C-3'

(SEQ ID NO: 59)
GP5-M: 5'-TTT NTN ACH GTD GTD GAY ACH AC-3'

(SEQ ID NO: 60)
GP6-M: 5'-GAA AHA TAA AYT GYA VDT CAW AYT C-3'
```

Wherein, N denotes A, C, T or G; H denotes A, C or T; D denotes A, G or T; Y denotes C or T; W denotes A or T; R denotes A or G; and V denotes A, C or G.

In the PCR reaction, 20 pmol of primers, 2.5 mM of dNTP mixture, 100 ng of genomic DNA, 5 µl of 10×PCR buffer (Solgent Co.), 2.5 units of Taq DNA polymerase (Solgent Co.), and 1 µl of 25 nM Cyanine-5-dUTP fluorescence substance were mixed to a final volume of 50 µl. The mixture was subjected to 35 PCR cycles, each cycle consisting of denaturation for 10 minutes at 94° C.; denaturation for 1 minute at 94° C.; annealing for 45 seconds at 55° C.; and extension for 45 seconds at 72° C. A final extension of 10 minutes at 72° C. was followed.

The PCR products labeled with Cy-5 were purified with a QuiaQuick PCR purification kit and concentrated to a final concentration of 25 µl, thus preparing DNA samples. The DNA samples were hybridized with the DNA chip for HPV diagnosis, prepared in the Example 2. In this hybridization, 3×SSC, 0.2% SDS, and 20 µg of salmon sperm DNA were mixed to a final volume of 40 µl, and the mixture was allowed to react at 50° C. for 2 hours.

After hybridization, the DNA chip washed with 2×SSC for 2 minutes, and with 0.2×SSC and 0.1% SDS (sodium dodecyl sulfate) for 5 minutes, and then two times with 0.2×SSC for 5 minutes each time. The washed chip was centrifuged at 700 rpm for 10 minutes, dried, and then scanned with an Axon 4000B scanner (Axon Instrument) to confirm the hybridization results.

The results of the HPV DNA chip test showed that, in the HPV-uninfected clinical sample, hybridization occurred only in the GAPDH gene (PCR control), but in the remaining clinical samples, hybridization occurred selectively in the PCR and positive controls and in portions on which probes containing sequences specific to HPV6, HPV16, HPV16 and 33 genotypes have been integrated (FIG. 7).

INDUSTRIAL APPLICABILITY

As described above, the present invention provides the producing method of the DNA chip that shows good signal intensity after hybridization without being influenced by the coating uniformity of a glass slide surface, as well as the DNA chip for HPV diagnosis produced thereby and the method for diagnosing the presence or genotype of HPV using the DNA chip. The inventive method for producing the DNA chip can solve the problems occurring in the prior art, in which a probe should be produced each time a DNA chip is produced, or primers should vary depending on the sequence of probes. Thus, the inventive method for producing the DNA chip is highly useful for the efficient production of DNA chips.

What we claimed is:

1. A method for producing a DNA chip, the method comprising the steps of:
   (a) ligating one or more double-helical probes into one or more vectors, wherein each probe comprises an oligonucleotide coupled to a linker at one or both ends, and wherein the oligonucleotide is a 60 bp by sequence specific to an HPV genotype, where a linker is coupled to both ends of an oligonucleotide to be integrated on a slide, into a vector;
   (b) transforming host cells with the vectors;
   (c) culturing the transformed host cells to recover a plurality of double-helical probes, each including the linker, wherein the linker is a part of the base sequence of the vector; and
   (d) integrating the plurality of double-helical probes on a slide to produce a DNA chip, wherein the double-helical probes of said plurality of double helical probes are selected from the group consisting of:
   (i) SEQ ID NOs: 1 and 2;
   (ii) SEQ ID NOs: 3 and 4;
   (iii) SEQ ID NOs: 5 and 6;
   (iv) SEQ ID NOs: 7 and 8;
   (v) SEQ ID NOs: 9 and 10;
   (vi) SEQ ID NOs: 11 and 12;
   (vii) SEQ ID NOs: 13 and 14;
   (viii) SEQ ID NOs: 15 and 16;
   (ix) SEQ ID NOs: 17 and 18;
   (x) SEQ ID NOs: 19 and 20;
   (xii) SEQ ID NOs: 21 and 22;
   (xiii) SEQ ID NOs: 23 and 24;
   (xiv) SEQ ID NOs: 25 and 26;
   (xv) SEQ ID NOs: 27 and 28;
   (xvi) SEQ ID NOs: 29 and 30;
   (xvii) SEQ ID NOs: 31 and 32;
   (xviii) SEQ ID NOs: 33 and 34;
   (xix) SEQ ID NOs: 35 and 36;
   (xx) SEQ ID NOs: 37 and 38;
   (xxi) SEQ ID NOs: 39 and 40;
   (xxii) SEQ ID NOs: 41 and 42;
   (xxiii) SEQ ID NOs: 43 and 44;
   (xxiv) SEQ ID NOs: 45 and 46;
   (xxv) SEQ ID NOs: 47 and 48;
   (xxvi) SEQ ID NOs: 49 and 50;
   (xxvii) SEQ ID NOs: 51 and 52; and
   (xxviii) SEQ ID NOs: 53 and 54; and wherein the DNA chip is effective in the identification of Human Papilloma Virus (HPV) infection and the genotype of HPV infection in a sample.

2. The method for producing a DNA chip according to claim 1, wherein the vector is a cloning vector.

3. The method for producing a DNA chip according to claim 2, wherein the cloning vector is a plasmid vector.

4. The method for producing a DNA chip according to claim 3, wherein the plasmid vector is a T-vector.

5. The method for producing a DNA chip according to claim 4, wherein the T-vector is pGEM T easy vector.

6. The method for producing a DNA chip according to claim 1, wherein the host cell is *E. coli*.

7. The method for producing a DNA chip according to claim 1, wherein the linker is coupled to both ends of the oligonucleotide, and has the length of 30-150 bp.

8. The method for producing a DNA chip according to claim 1, wherein the linker is a part of the base sequence of a T-vector.

9. The method of claim 1, wherein the genotype of HPV infection is any of HPV16, HPV18, HPV31, HPV33, HPV35, HPV39, HPV45, HPV51, HPV52, HPV54, HPV56, HPV58, HPV59, HPV66, HPV6, HPVII, HPV34, HPV40, HPV42, HPV43, HPV44, HPV62, HPV67, HPV68, HPV69, HPV70, and HPV72.

* * * * *